United States Patent [19]
Miura et al.

[11] Patent Number: 4,675,134
[45] Date of Patent: Jun. 23, 1987

[54] PROCESS FOR PRODUCING IMINOCTADINE 3-ALKYLBENZENESULFONATES

[75] Inventors: Yasuhisa Miura, Hazaki; Yasuki Kataoka; Tohru Asada, both of Shisui, all of Japan

[73] Assignee: Dainippon Ink and Chemicals, Inc., Tokyo, Japan

[21] Appl. No.: 887,337

[22] Filed: Jul. 21, 1986

[30] Foreign Application Priority Data

Jul. 23, 1985 [JP]  Japan ................................ 60-161202

[51] Int. Cl.$^4$ .......................................... C07C 129/00
[52] U.S. Cl. .............................................. 260/501.14
[58] Field of Search ................................... 260/501.14

[56] References Cited

U.S. PATENT DOCUMENTS

| 2,394,003 | 2/1946 | Newbery et al. | 260/501.14 |
| 2,410,796 | 11/1946 | Newbery et al. | 260/501.14 |
| 2,424,325 | 7/1947 | Newbery et al. | 260/501.14 |
| 2,473,112 | 6/1949 | Short et al. | 260/501.14 |
| 3,105,853 | 10/1963 | McKay et al. | 260/501.14 |
| 3,799,988 | 3/1974 | Hashimoto et al. | 260/501.14 |
| 4,339,459 | 7/1982 | Diery et al. | 260/501.14 |

Primary Examiner—Paul J. Killos
Attorney, Agent, or Firm—Sherman and Shalloway

[57] ABSTRACT

A process for producing iminoctadine 3-alkylbenzenesulfonates, which comprises reacting triamine of the formula $H_2N(CH_2)_8NH(CH_2)_8NH_2$ with an O-alkylisourea alkylbenzenesulfonate in the presence or absence of a reaction medium.

6 Claims, No Drawings

PROCESS FOR PRODUCING IMINOCTADINE 3-ALKYLBENZENESULFONATES

This invention relates to a process for producing iminoctadine 3-alkylbenzenesulfonates (to be referred to as iminoctadine ABS salts) represented by the folllowing formula

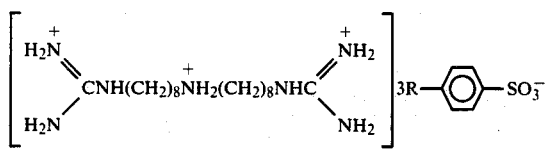

which are among acid addition salts of 1,1'-iminodi(octamethylene)diguanidine (iminoctadine by ISO nomenclature; formerly called guazatine) useful as agricultural-horticultural fungicides but which have reduced phytotoxicity to useful plants, by reacting triamine of the formula $H_2N(CH_2)_8NH(CH_2)_8NH_2$ with O-alkylisourea alkylbenzenesulfonates (to be referred to as O-alkylisourea ABS salts).

The present applicant previously filed applications for patent on water-insoluble acid addition salts of guanidine compounds in an attempt to eliminate or reduce the strong phytotoxicity to specific crops, which is the only defect of guanidine-type fungicides (EP 85101711.1, US 705,365, CA No. 474511, China No. 85101560, Taiwan No. 14100683 and Korea No. 1149/85). Iminoctadine ABS salts which come within these salts and have especially superior fungicidal efficacy and reduced phytotoxicity and toxicity can be produced by salt exchange of iminoctadine triacetate generally in practical use. The pesent inventor obtained a patent on a process for producing the iminoctadine triacetate (Japanese Patent Publication No. 35907/1982).

Addition of a stoichiometrically excessive amount of an alkylbenzenesulfonic acid to an aqueous solution of iminoctadine triacetate liberates acetic acid. Since the resulting iminoctadine ABS salt is a water-insoluble viscous substance, acetic acid cannot be sufficiently removed even when the reaction product is concentrated to dryness. It may be possible to extract and wash the reaction product, but no suitable extractant is available. Even when sodium acetate is formed by using a sodium alkylbenzenesulfonate, a suitable extractant is not available and part of sodium acetate inevitably remains. Since the remaining acetate decreases the effect of alleviating phytotoxicity, these methods are not satisfactory.

It might be possible on the other hand to use a method which comprises reacting iminoctadine triacetate with sodium carbonate to form guazatine sesquicarbonate having good crystallinity, washing it with water to remove sodium acetate completely, and then adding an alkylbenzenesulfonic acid. However, this method also requires a salt exchanging step, and the operation is troublesome. Particularly, when the method goes throu9h the sesquicarbonate, the desired active components will be lost during filtration and washing of the sesquicarbonate.

The present inventors have made extensive investigations in order to overcome these difficulties, and have now found that by using O-alkylisourea ABS salts hitherto unknown as a guanidinating agent for triamine, iminoctadine ABS salts ar obtained in high yields by a simple operation.

The present invention provides a process for producing iminoctadine 3-alkylbenzenesulfonates, which comprises reacting triamine represented by the formula $H_2N(CH_2)_8NH(CH_2)_8NH_2$, i.e. 1,17-diamino-9-azaheptadecane.

The O-alkylisourea ABS salts used in this invention can be produced in quantitative yields from cyanamide, alkylbenzenesulfonic acids and lower alcohols such as methanol, ethanol or propanol.

The amount of the O-alkylisourea ABS salt used in the process of this invention is generally 2 to 4 moles, preferably 2.06 to 2.40 moles, per mole of triamine.

Preferred alkylbenzenesulfonic acids used in this invention are those having 1 to 20 carbon atoms, especially 4 to 18 carbon atoms, in the alkyl moiety. Dodecylbenzenesulfonic acid is especially preferred.

Commercial dodecylbenzenesulfonic acid marketed as an industrial material can be preferably used in this invention since it is a mixture of alkylbenzenesulfonic acids in which the alkyl groups have 10 to 14 carbon atoms, mainly 12 carbon atoms.

Water or a mixture of water and methanol is used as the reaction medium in the process of this invention. The reaction may be carried out by mixing triamine with the O-alkylisourea ABS salt. To inhibit the formation of by-products, it is preferred to add the O-alkylisourea ABS salt or its solution in the reaction medium dropwise over the course of 1 to 10 hours to a solution of triamine in the reaction medium. The reaction temperature may generally be selected from the range of 0° to 100° C., preferably 20° to 30° C. At the preferred reaction temperatures, the selectivity of the reaction is excellent. The reaction time varies depending upon the reaction temperature. Under preferred conditions, the reaction is terminated within 10 hours after the addition, and the yield of the final product is 93 to 95 mole % based on triamine when O-methylisourea ABS salts are used. The O-alkylisourea ABS salts, whether the O-alkyl group is an O-methyl, ethyl or propyl group, i.e., $O-C_{1-3}$ alkylisourea ABS salts, are operable under the reaction conditions described above, but the yield of the final product decreases in the order of methyl, ethyl and propyl in the O-alkyl group.

The iminoctadine ABS salt once formed is very stable, and prolongation of the reaction time would not adversely affect it.

The outstanding feature of the present invention is that iminoctadine ABS salts having reduced phytotoxicty can be obtained in very high yields in one step from triamine.

The following examples specifically illustrate the present invention. All percentages in these examples are by weight.

EXAMPLE 1

Water (90.0 g) and 60.0 g of methanol were added to 54.3 g (0.196 mole) of 98% triamine, and with stirring, 266.6 g (0.42 mole) of a 65.1% methanol solution of O-methylisourea methylisourea dodecylbenzenesulfonate was added dropwise at 20° to 25° C. over the course of 3 hours. After the addition, the mixture was stirred at 20° to 25° C. for 10 hours. Then, 62.8 g (0.2 equivalent) of dodecylbenzenesulfonic acid (acid value 178.7 mg KOH/g) was added, and the mixture was further stirred for 30 minutes. On standing, the mixture separated into two layers. The lower layer was taken, and analyzed by liquid chromatography. The analysis showed the formation of 247.8 g of iminoctadine dodecylbenzenesulfonate. The yield was 94.7 mole % based on triamine.

COMPARATIVE EXAMPLE 1

A 40% aqueous solution of O-methylisourea acetate (140.8 g; 0.42 mole) was added to 54.3 g (0.196 mole) of 98% triamine and 150.0 g of water, and the mixture was stirred at 20° to 25° C. for 10 hours. Acetic acid (12.0 g; 0.2 mole) was added, and the reaction mixture was analyzed by liquid chromatography. It was found that 99.8 g of iminoctadine triacetate was formed in a yield of 95.0 mole % based on triamine.

A 25% aqueous solution of sodium carbonate (508.8 g; 1.2 moles) was stirred at 70° to 80° C., and the iminoctadine triacetate-containing reaction mixture obtained above was poured into the aqueous solution. The mixture was stirred for 30 minutes and then cooled to room temperature. The crystals precipitated were separated by filtration, and washed with water. Furthermore, 400 g of water was added, and the mixture was stirred at 70° to 80° C. for 30 minutes, and cooled to room temperature. The crystals were separated by filtration, washed with water, and dried overnight at 60° C. to give 85.0 g of a white powder. Liquid chromatography showed that the iminoctadine sesquicarbonate had a purity of 93.2%. By potentiometric titration, the equivalent weight of the guanidino group and the amino group was 388.6 mg KOH/g.

Methanol (300 ml) was added to 85.0 g of iminoctadine sesquicarbonate, and with stirring at 50° C., 184.9 g of dodecylbenzenesulfonic acid (acid value 178.7 mg KOH/g) was added dropwise. The mixture was cooled to room temperature, and the reaction mixture was analyzed by liquid chromatography. It was found that 235.7 g of iminoctadine dodecylbenzenesulfonate formed, and its yield based on triamine was 90.1 mole %.

What is claimed is:

1. A process for producing iminoctadine 3-alkylbenzenesulfonates, which comprises reacting triamine of the formula $H_2N(CH_2)_8NH(CH_2)_8NH_2$ with an O-alkylisourea alkylbenzenesulfonate in the presence or absence of a reaction medium.

2. The process of claim 1 wherein a solution of the O-alkylisourea alkylbenzenesulfonate in the reaction mixture is added dropwise to a solution of triamine in the reaction medium.

3. The process of claim 1 wherein the O-alkylisourea alkylbenzenesulfonate is an O—$C_{1-3}$ alkylisourea alkylbenzenesulfonate.

4. The process of claim 1 wherein the O-alkylisourea alkylbenzenesulfonate is an O-alkylisourea $C_{4-18}$ alkylbenzenesulfonate.

5. The process of claim 1 whrein the O-alkylisourea alkylbenzenesulfonate is O-methylisourea dodecylbenzenesulfonate.

6. The process of claim 2 wherein the solution of the O-alkylisourea alkylbenzenesulfonate in the reaction medium is added dropwise at 20° to 30° C. over the course of 1 to 10 hours.

* * * * *